United States Patent [19]

Clausen

[11] Patent Number: 4,473,375
[45] Date of Patent: Sep. 25, 1984

[54] COMPOSITION AND METHOD FOR THE COLORING OF HAIR

[75] Inventor: Thomas Clausen, Weiterstadt, Fed. Rep. of Germany

[73] Assignee: Wella Aktiengesellschaft, Darmstadt, Fed. Rep. of Germany

[21] Appl. No.: 405,339

[22] Filed: Aug. 5, 1982

[30] Foreign Application Priority Data

Aug. 20, 1981 [DE] Fed. Rep. of Germany ....... 3132885

[51] Int. Cl.³ ............................................... A61K 7/13
[52] U.S. Cl. ........................................................ 8/409
[58] Field of Search ........................................... 8/409

[56] References Cited

U.S. PATENT DOCUMENTS 3,231,471  1/1966  Lange ...................... 8/409

FOREIGN PATENT DOCUMENTS 1492158  1/1970  Fed. Rep. of Germany .......... 8/409
2445002  4/1975  Fed. Rep. of Germany .
2714831  10/1978  Fed. Rep. of Germany .......... 8/409
1398193  3/1965  France .................................. 8/409
1436304  5/1976  United Kingdom .

*Primary Examiner*—Albert T. Meyers
*Assistant Examiner*—John M. Kilcoyne
*Attorney, Agent, or Firm*—Michael J. Striker

[57] ABSTRACT

A composition and method for the oxidative coloring of hair are disclosed, on the basis of a developer substance-coupler substance combination, whereby as coupler substance at least one 3,5-diaminopyridine derivative of the general Formula

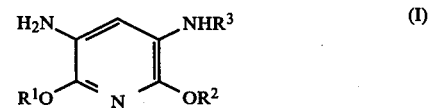

in which $R^1$ and $R^2$ independent of each other are $CH_3$, $C_2H_5$ or $C_2H_4OH$ and $R^3$ is hydrogen, $C_1$-$C_4$-alkyl or $C_1$-$C_4$-hydroxyalkyl, also in the form of the physiologically compatible salt, is used. The coupler substance, 3,5-diamino-2,6-dimethoxypyridine being preferred, should be present in the hair coloring composition in a concentration from 0.01 to 3.0% by weight, preferably 0.1 to 2.0% by weight. The coupler substances according to Formual I are storage-stable, well soluble in water, and have toxicologically as well as dermatologically favorable characteristics. The coupler substances according to Formula I produce in combination with 1,4-diaminobenzene or its derivatives very intensive blue-black tones without red portions, and in combination with 4-aminophenol, strongly lustrous gold-orange tones.

13 Claims, No Drawings

COMPOSITION AND METHOD FOR THE COLORING OF HAIR

BACKGROUND OF THE INVENTION

The subject of the invention are a composition and method for the oxidative coloring of hair, on the basis of developer and coupler substances, whereby a derivative of 3,5-diaminopyridine is used as coupler substance.

Oxidation dyes have acquired a substantial significance for hair coloration. The coloration is produced through reaction of determined developer substances with determined coupler substances in the presence of a suitable oxidation agent.

As developer substances, preferably 2,5-diaminotoluene, 4-aminophenol and 1,4-diaminobenzene are used, but also 2,5-diaminoanisole, 2,5-diaminobenzyl alcohol and 2-($\beta$-hydroxyethyl)-1,4-diaminobenzene have attained a certain importance. In certain cases also tetraaminopyrimidine can be used as developer substance. The preferably used coupler substances are $\alpha$-naphthol, resorcin, 4-chloro-resorcin, m-aminophenol, 5-amino-o-cresol and derivatives of m-phenylene diamine such as 2,4-diaminophenetol and 2,4-diaminoanisole. These derivatives as well as the m-phenylenediamine itself, on account of their capacity to produce blue tones upon the oxidative coupling with 1,4-diaminobenzene or 1,4-diaminobenzene derivatives, have acquired importance as so-called blue couplers.

Numerous particular standards have been set for oxidation dyes which are used for the coloring of human hair. They must be unobjectionable as to toxicology and dermatology and make possible the production of colorations, i.e. shades, hues, in the desired intensity. It is furthermore necessary that through combination of suitable developer and coupler components a wide range of different color tints can be produced. The resulting coloring should, to a good degree, be fast to light and resistant to permanent-wave treatment, acids and rubbing. Such colorings must, at any rate, remain stable against the influence of light, rubbing and chemical agents, for a period of at least 4 to 6 weeks.

The m-phenylenediamine, its derivatives 2,4-diaminotoluene and 2,4-diaminoanisole, presently used as blue couplers in hair coloring compositions, as well as also blue couplers recommended in more recent times, such as for example 1-hydroxy-3-amino-6-chlorobenzene and 2,4-diaminophenoxyethanol, cannot however satisfactorily fulfill the previously mentioned requirement.

SUMMARY OF THE INVENTION

It is therefore an object of the present invention to make available a hair coloring composition as well as a method of hair coloring, with which the requirements set are better fulfilled.

To this end it has now been discovered that agents for the oxidative coloring of hair on the basis of a developer substance-coupler substance combination, as well as if necessary other customary coloring components and customary additives, thereby characterized in that they contain as coupler substance at least one 3,5-diaminopyridine derivative of the general Formula I

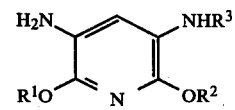

whereby $R^1$ and $R^2$ independently of each other signify $CH_3$, $C_2H_5$ or $C_2H_4OH$ and $R^3$ represents hydrogen, $C_1-C_4$-alkyl or $C_1-C_4$-hydroxyalkyl, also in the form of the physiologically compatible salts, do justice to this object in outstanding degree.

The 3,5-diaminopyridine derivative of Formula I, contained as coupler substance in the hair coloring composition according to the present invention, such as for example 3,5-diamino-2,6-dimethylpyridine, 3,5-diamino-2,6-diethyoxypyridine and 3,5-diamino-2,6-di-($\beta$-hydroxyethyloxy)-pyridine, are well soluble in water. They display moreover an excellent storage ability, particularly as component of the here described hair coloring composition.

The coupler substance according to the present invention in the hair coloring composition, of which the 3,5-diamino-2,6-dimethoxypyridine is preferred, should be contained in a concentration from about 0.01 up to 3.0% by weight, preferably 0.1 to 2.0% by weight.

Moreover, additional known coupler substances can be contained in the hair coloring composition, in particular resorcin, 4-chlorresorcin, 2-methylresorcin, 2-amino-4-($\beta$-hydroxyethylamino)-anisol, 2,4-diaminophenyl-ethanol, 2,4-diaminophenoxyethanol, 1,5-dihydroxytetralin, m-aminophenol, 3-amino-2-methylphenol, 3-amino-6-methylphenol, 4-hydroxy-1,2-methylene dioxybenzene, 4-amino-1,2-methylene dioxybenzene, 2,4-diaminoanisol and 2,4-diaminophenetol.

Above all, 1,4-diaminobenzene, 2,5-diaminotoluene, 2,5-diaminoanisole, 2,5-diaminobenzyl alcohol, 3-methyl-4-aminophenol and 4-aminophenol of the known developer substances come into consideration as component of the hair coloring composition according to the present invention.

The mentioned coupler and developer substances can be contained in the hair coloring composition individually or in mixture with one another.

The total amount of developer substance-coupler substance combination contained in the herein described hair coloring composition should come to about 0.1 to 5.0% by weight, preferably 0.5 to 3.0% by weight.

The developer components are generally employed in about equimolar amounts, relative to the coupler component. It is, however, not disadvantageous if the developer component is provided in a certain excess or deficiency. Particularly for the production of more mat or weaker, dull tint, it can if necessary be favorable to use the developer component in a deficient amount.

In addition, the hair coloring composition according to the present invention can contain other coloring components, for example 6-amino-2-methylphenol, 6-amino-3-methylphenol and 6-amino-3-ethoxyphenol, as well as further customary direct-drawing colorants, for example triphenolmethane colorants such as Diamond Fuchsin (C. I. 42 510) and Leather Ruby HF (C. I. 42 520), aromatic nitro colorants, such as 2-nitro-1,4-diaminobenzene, 2-amino-4-nitrophenol and 2-amino-5-nitrophenol, azo dyes such as Acid Brown 4 (C. I. 14 805) i.e. 7-(4'-aminophenylazo)-4-sulfo-8-hydroxynaphthalene sodium salt and Acid Blue 135 (C. I. 13

385), anthraquinone dyes such as Disperse Red 15 (C. I. 60 710) i.e. 1-amino-4-hydroxy-9,10-anthracenedione and Disperse Violet 1 (C. I. 61 100) 1,4-diamino-9,10-anthracenedione, moreover 1,4,5,8-tetraaminoanthraquinone and 1,4-diaminoanthraquinone.

The above-given commercially identified colorants are, respectively, the following chemicals: 4,4',4"-triamino-3-methyl-triphenylcarbenium-chloride; 4,4',4"-triamino-3,3',3"-trimethyl-triphenyl-carbenium-chloride; 7-(4'-amino-phenylazo)-4-sulfo-8-hydroxy-naphthalene sodium salt; 1-phenylamino-4-(1-hydroxy-5-sulfo-8-napthaleneazo)-napthalene-8-sulfonic acid disodium salt; 1-amino-4-hydroxy-9,10-anthracenedione; and 1,4-diamino-9,10-anthracenedione.

Obviously the coupler and developer substances as well as also other coloring components can be used, to the extent that they are bases, in the form of the physiologically compatible acid addition salt, such as for example as hydrochloride or sulfate or, to the extent that they possess aromatic OH groups, in the form of the salt with bases, for example as alkali phenolate.

Beyond that, there can be present in the hair coloring compositions still further customary cosmetic additives, for example antioxidants such as ascorbic acid or sodium sulfite, perfume oils, complex formers, wetting agents, emulsifiers, thickeners, hair care substances, among others.

The form of the preparation can, for example, be a solution, particularly an aqueous or water-alcohol solution. The particularly preferred preparations forms are however a cream, a gel or an emulsion. Their composition represents a mixture of the dye components with the additives typical for such preparations.

Customary additives in solutions, creams, emulsions or gels are, for example, solvents such as water, lower aliphatic alcohols, for example ethanol, propanol and isopropanol, or glycols such as glycerine and glycol ethers such as propylene glycol, wetting agents or emulsifiers from the classes of anionic, cationic, amphoteric or non-ionogenic surface-active substances such as fatty alcohol sulfates, alkyl sulfonate, alkylbenzene sulfonate, alkyltrimethylammonium salt, alkylbetaine, oxethylated fatty alcohol, oxethylated nonylphenol, fatty acid alkanolamide, oxethylated fatty acid ester, thickeners such as higher fatty alcohols, starch, cellulose derivatives, vaseline, paraffin oil and fatty acids as well as hair care substances such as lanolin derivatives, cholesterin, pantothenic acid and betaine. The mentioned components are used in amounts customary for such purposes, for example the wetting agents and emulsifiers can be contained in the preparations in concentrations from about 0.5 to 30% by weight, whereas the thickeners can be contained in amounts from about 0.1 to 25% by weight.

Indeed, according to composition, the hair coloring agents of the present invention can react weakly acid, neutral or alkaline. In particular, they display a pH-value in the alkaline range between 8.0 and 11.5, whereby the adjustment follows preferably with ammonia. However, also organic amines, for example monoethanolamine and triethanolamine, or also inorganic bases such as sodium hydroxide and potassium hydroxide, can be used.

With the method according to the present invention for the oxidative coloration of hair, one mixes the hair coloring composition on the basis of a developer substance-coupler substance combination as well as if necessary other customary coloring components and customary additives, thereby characterized in that they contain as coupler substance at least one 3,5-diaminopyridine derivative of the general Formula I

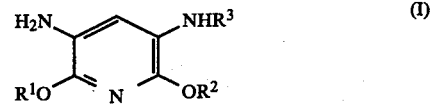

whereby $R^1$ and $R^2$ independent of one another signify $CH_3$, $C_2H_5$ or $C_2H_4OH$ and $R^3$ represents hydrogen, $C_1$–$C_4$-alkyl or $C_1$–$C_4$-hydroxyalkyl, also in the form of the salts, shortly before use, with an oxidation agent, and this mixture is applied onto the hair. As oxidation agent for the development of the hair coloring, mainly hydrogen peroxide, for example as 6% aqueous solution or its additive compounds with urea, melamine or sodium borate, come into consideration. The mixture is allowed to act on the hair at 15° to 50° C. for about 10 to 45 minutes, preferably 30 minutes. The hair is then rinsed with water and dried. In given instances, washing with shampoo is performed after this rinse, and a final rinse is made with a weak organic acid, such as for example citric acid or tartaric acid.

The production of the 3,5-diaminopyridine derivative contained in the described hair coloring composition is known. Appropriate information can be obtained, for example, from German Offenlegungsschrift No. 2 445 002.

According to a further route of synthesis, the 2,6-dichloro- or 2,6-dibromopyridine are used as starting material. By nucleophilic substitution of the halogen through the corresponding alcoholate and subsequent nitration, one obtains according to the following reaction scheme the corresponding 3,5-dinitro-2,6-dialkoxypyridine (III). Finally, the so obtained dinitro compound is converted into the desired 3,5-diamino-2,6-dialkoxy compound (IV) through reduction of the nitro groups.

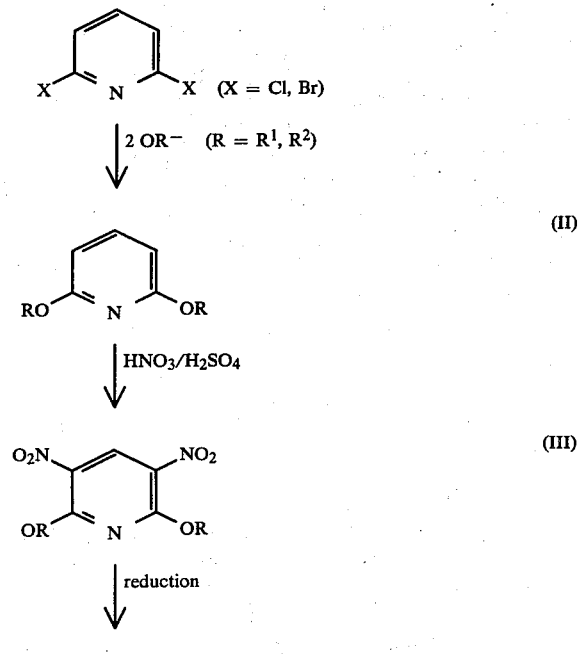

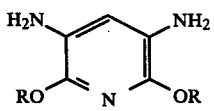

(IV)

The corresponding N-substituted derivatives of the 3,5-diamino-2,6-dialkoxypyridine is likewise acceptable according to typical synthesis steps described in the preparative organic chemistry literature. The 2,6-dialkoxypyridine compound (II) is initially mononitrated, and subsequently the nitro groups are reduced to amino groups. The monoalkylation of the amine nitrogen follows. Through renewed nitration and subsequent reduction of the nitro groups into amino groups, one obtains the final product.

With regard to the coloring possibilities, the hair coloring composition according to the present invention, indeed according to type and composition of the coloring components, offers a wide range of different color tints, which run from blonde through brown, ash, mat, golds, even to blues and black color tones. Herewith the color tones distinguish by their particular color intensity and light-fastness.

Of more significance is the advance obtained through the use of the 3,5-diaminopyridine derivative of the given Formula I in the hair coloring compositions according to the present invention in a toxicological and dermatological sense, for example in contrast to the known blue couplers 2,4-diaminotoluene, 2,4-diaminoanisole and m-phenylenediamine. Thus the coupler substance 3,5-diamino-2,6-dimethoxypyridine according to the present invention showed in the Ames Test, in contrast to 2,4-diaminotoluene or 2,4-diaminoethylbenzene, no mutagenic activity in Salmonella typhimurium stock.

The pyridine derivatives according to the present invention produce, as coupler substances in combination with the developer substances 1,4-diaminobenzene and its derivatives, very intensive blue-black tones without red portions, such as cannot be obtained with the coupler substances previously known for use in hair coloring compositions, such as for example 2,4-diaminotoluene, 2,4-diaminoanisole, 2,4-diaminophenoxyethanol, 2,6-diaminotoluene, 2-amino-4-(β-hydroxyethylamino)-anisole or 3-amino-6-chlorophenol.

The blue coupler unconditionally necessary for the production of mat and ash tones yields namely with the previously mentioned 1,4-diamino compounds as developer substances red or violet blue tones, so that the achievement of ash and mat tones is impossible or made very much more difficult. In contrast, it is now possible, without problems, on account of the advantageous characteristics of the pyridine derivatives according to the present invention, to produce blue tones without red portions, to color the hair permanently in ash or mat natural tones, which also remain stable in light and do not fade to red as the tints produced with m-phenylenediamine.

A further advantage of the 3,5-diaminopyridine derivative contained in the hair coloring composition according to the present invention exists in the broad spectrum of producible color tones. Thus, for example, in combination with 4-aminophenol as developer substance, strongly lustrous, fashionable gold-orange tones are produced, for the production of which previously mixtures of different couplers had to be employed.

Finally, it is possible with the aid of the hair coloring composition according to the present invention to also provide a coloring of grayed, chemically undamaged hair, without problems and with very good covering power.

The novel features which are considered characteristic for the invention are set forth in particular in the appended claims. The invention itself, however, both as to its construction and its method of operation, together with additional objects and advantages thereof, will be best understood from the following description of specific embodiments.

EXAMPLE 1

| Hair Coloring Composition in Gel Form | |
|---|---|
| 0.75 g | 3,5-diamino-2,6-dimethoxypyridine-dihydrochloride |
| 0.70 g | 2,5-diaminotoluene sulfate |
| 0.30 g | ascorbic acid |
| 1.00 g | hydroxyethylcellulose, highly viscous |
| 5.00 g | laurylalcohol-diglycolethersulfate sodium salt (28% aqueous solution) |
| 10.00 g | ammonia, 22% |
| 82.25 g | water |
| 100.00 g | |

50 g of the above hair coloring composition are mixed with 50 ml hydrogen peroxide solution (6%) shortly before use, and the mixture is then applied to white human hair. After a period of 30 minutes at about 40° C., the hair is rinsed with water and the dried. The hair is colored a deep blue-black.

EXAMPLE 2

| Hair Coloring Composition in Gel Form | |
|---|---|
| 0.5 g | 2,6-di-(β-hydroxyethyloxy)-3,5-diaminopyridine-dihydrochloride |
| 0.5 g | 2,5-diaminotoluene sulfate |
| 0.3 g | ascorbic acid |
| 1.0 g | hydroxyethylcellulose, high viscosity |
| 5.0 g | laurylalcohol-diglycolether sulfate sodium salt (28% aqueous solution) |
| 10.0 g | ammonia, 22% |
| 82.7 g | water |
| 100.0 g | |

50 g of the above hair coloring composition are mixed with 50 ml hydrogen peroxide solution (6%) shortly before use, and then applied onto blonde human hair. After a reaction period of 30 minutes at 40° C., the hair is rinsed with water and then dried. The hair is colored an intensive blue tone.

EXAMPLE 3

| Hair Coloring Composition in Gel Form | |
|---|---|
| 0.08 g | 3,5-diamino-2,6-dimethoxypyridine-dihydrochloride |
| 0.30 g | 1,4-diaminobenzene |
| 0.25 g | resorcin |
| 0.30 g | ascorbic acid |
| 15.00 g | oleic acid |
| 7.00 g | isopropanol |
| 10.00 g | ammonia, 22% |
| 67.07 g | water |

-continued

| Hair Coloring Composition in Gel Form |
|---|
| 100.00 g |

50 g of this hair coloring composition are mixed with 50 ml hydrogen peroxide solution (6%) shortly before use, and the mixture is allowed to work itself into white human hair for 30 minutes at 40° C. Thereafter, the hair is rinsed with water and then dried. The hair has obtained a naturally effective medium mat blonde coloration.

EXAMPLE 4

| Hair Coloring Composition in Cream Form | |
|---|---|
| 0.60 g | 3,5-diamino-2,6-dimethoxypyridine-dihydrochloride |
| 0.30 g | 4-aminophenol |
| 0.30 g | sodium sulfite, water-free |
| 3.50 g | laurylalcohol-diglycolethersulfate sodium salt (28% aqueous solution) |
| 15.00 g | cetyl alcohol |
| 3.00 g | ammonia, 22% |
| 77.30 g | water |
| 100.00 g | |

50 g of this hair coloring composition are mixed with 50 ml hydrogen peroxide solution (6%) shortly before use, and the mixture is subsequently applied onto white human hair. After a period of 30 minutes at 40° C., the hair is rinsed initially with water, then with a dilute citric acid solution, and subsequently dried. The hair is colored in a fashionable gold-orange color tone.

All percent numbers herein represent by weight.

It will be understood that each of the elements described above, or two or more together, may also find a useful application in other types of hair treatments differing from the types described above.

While the invention has been illustrated and described as embodied in a composition and method for the coloring of hair, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. Composition for the oxidative coloring of human hair on the basis of 0.1 to 5.0% by weight of a developer substance-coupler substance combination comprising as coupler substance 0.01 to 3.0% by weight of at least one 3,5-diaminopyridine derivative of formula I

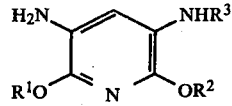

wherein $R^1$ and $R^2$ are the same or different and are each $CH_3$, $C_2H_5$ or $C_2H_4OH$ and $R^3$ is hydrogen, $C_1$–$C_4$-alkyl or $C_1$–$C_4$-hydroxyalkyl, or a physiologically compatible salt thereof.

2. Composition according to claim 1, containing the coupler substance of the general formula I or a physiologically compatible salt thereof in an amount between 0.1 and 2.0% by weight.

3. Composition according to claim 1, containing as coupler substance 3,5-diamino-2,6-dimethoxypyridine.

4. Composition according to claim 1, further comprising an additional coupler substance which is resorcin, 4-chlororesorcin, 2-methylresorcin, 2-amino-4-(β-hydroxyethylamino)-anisole, 2,4-diaminophenylethanol, 2,4-diaminophenoxyethanol, 2,4-diaminoanisole, 2,4-diaminophenetol, 1,5-dihydroxytetralin, m-aminophenol, 3-amino-2-methylphenol, 3-amino-6-methylphenol, 4-hydroxy-1,2-methylenedioxybenzene or 4-amino-1,2-methylenedioxybenzene.

5. Composition according to claim 1, wherein said developer substance is 1,4-diaminobenzene, 2,5-diaminotoluene, 2,5-diaminoanisole, 2,5-diaminobenzyl alcohol, 3-methyl-4-aminophenol or 4-aminophenol.

6. Composition according to claim 1, wherein the amount of said developer substance-coupler substance combination is from 0.5 to 3.0% by weight.

7. Composition according to claim 1, further comprising an antioxidant.

8. Composition according to claim 7, wherein said antioxidant is ascorbic acid or sodium sulfite.

9. Composition according to claim 1, further comprising an additive which is water, lower aliphatic alcohol, oxethylated nonylphenol, starch, chloesterin, pantothenic acid, betaine, sodium hydroxide, potassium hydroxide, ammonia, monoethanolamine or triethanolamine.

10. Composition according to claim 1, having a pH-value from about 8.0 to about 11.5.

11. Method for the oxidative coloring of hair, comprising applying a hair coloring composition according to claim 1, after addition of hydrogen peroxide or its additive compounds with urea, melamine or sodium borate, to the hair, allowing said hair coloring composition to act on the hair for about 10 to 45 minutes at a temperature from about 15° to 50° C., rinsing the hair and then drying the hair.

12. Method according to claim 11, further comprising after said rinsing said hair and before said drying said hair, washing and after-rinsing said hair.

13. Composition according to claim 1, further comprising a coloring component selected from the group consisting of 6-amino-2-methylphenol, 6-amino-3-methylphenol, 6-amino-3-ethoxyphenol, 4,4',4"-triamino-3-methyl-triphenyl carbeniumchloride, 4,4',4"-triamino-3,3',3"-trimethyl-triphenylcarbeniumchloride, 2-nitro-1,4-diaminobenzene, 2-amino-4-nitrophenol, 2-amino-5-nitrophenol, 7-(4'-amino-phenylazo)-4-sulfo-8-hydroxynaphthalene sodium salt, 1-phenylamino-4-(1-hydroxy-5-sulfo-8-naphthaleneazo)-naphthalene-8-sulfonic acid disodium salt, 1-amino-4-hydroxy-9,10-anthracenedione, 1,4-diamino-9,10-anthracenedione, 1,4,5,8-tetraamino-anthraquinone and 1,4-diamino anthraquinone.

* * * * *